Figure 1:
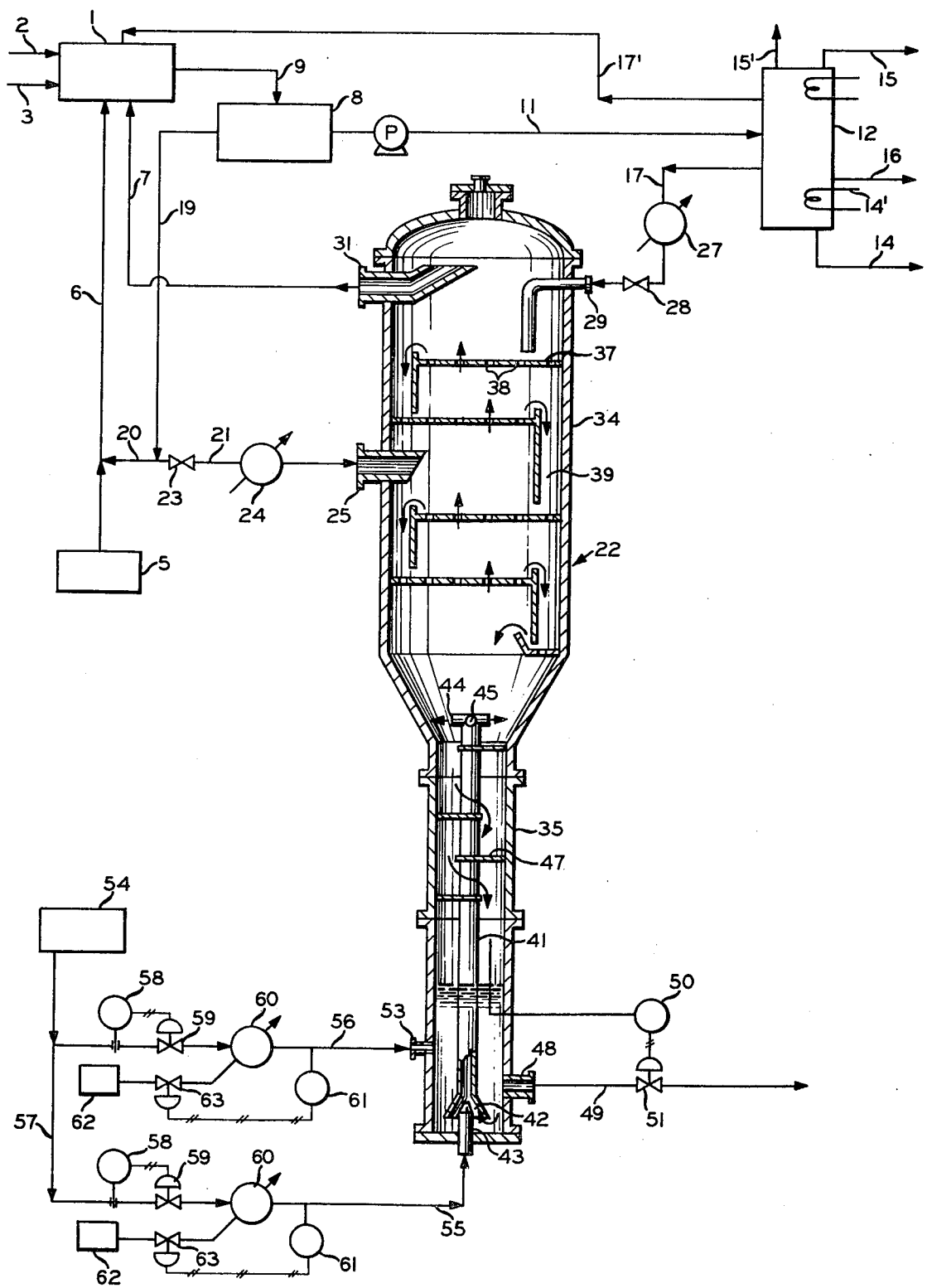

United States Patent [19]

Brown, Jr.

[11] 4,014,953
[45] Mar. 29, 1977

[54] METHOD FOR PURIFYING HF CATALYST IN AN ISOPARAFFIN-OLEFIN ALKYLATION

[75] Inventor: Webster W. Brown, Jr., Houston, Tex.

[73] Assignee: Phillips Petroleum Company, Bartlesville, Okla.

[22] Filed: Apr. 22, 1976

[21] Appl. No.: 679,283

Related U.S. Application Data

[62] Division of Ser. No. 547,261, Feb. 5, 1975, Pat. No. 3,975,164.

[52] U.S. Cl. .......................................... 260/683.48
[51] Int. Cl.² .......................................... C07C 3/54
[58] Field of Search ................ 260/683.48, 683.41, 260/683.58

[56] References Cited

UNITED STATES PATENTS

| | | | |
|---|---|---|---|
| 3,410,759 | 11/1968 | Fontenot et al. | 260/683.48 |
| 3,749,753 | 7/1973 | Skraba | 260/683.48 |
| 3,793,264 | 2/1974 | Chapman | 260/683.48 |

Primary Examiner—George Crasanakis

[57] ABSTRACT

An apparatus and process for separating acid soluble oil (ASO) from HF to purify same for reuse. The apparatus includes an alkylation HF rerun tower having an upper chamber and a lower chamber with liquid-vapor contact means in the upper chamber and an eductor and liquid-vapor contact means in the lower chamber. A stream of HF catalyst containing ASO is introduced into the upper chamber and is intimately contacted with an isoparaffin for separation of the HF and ASO. The ASO is collected in the lower chamber and is circulated through same and the eductor during which same is contacted by a vaporous isoparaffin for further separation of HF and ASO.

4 Claims, 1 Drawing Figure

METHOD FOR PURIFYING HF CATALYST IN AN ISOPARAFFIN-OLEFIN ALKYLATION

This is a division of application Ser. No. 547,261, filed Feb 5, 1975, now U.S. Pat. No. 3,975,164, which issued on Aug. 17, 1976.

In the petroleum industry it is common to produce high octane motor fuel by alkylating olefins with isoparaffins in the presence of hydrogen fluoride (HF) catalyst. The effluent from the alkylation reactor is usually passed to a settling vessel wherein a liquid hydrocarbon phase is separated from a liquid acid phase. The hydrocarbon phase is fractionated to separate low boiling hydrocarbons from the alkylate product. The acid phase is recycled to the reactor. However, it is necessary to purify a portion of the recycled acid in order to prevent an excessive buildup of acid soluble oil (ASO) in the system. This purification is usually accomplished by passing HF containing stream from the settler to a purification column or HF catalyst rerun column in which HF is stripped from the ASO by means of contacting same with a vaporous hydrocarbon or isoparaffin such as isobutane. A system for HF purification is disclosed in U.S. Pat. No. 3,793,394 issued to C. C. Chapman on Feb. 19, 1974. While such systems have been fairly effective when the system contains an externally located eductor for recycle of ASO to the column, same has a tendency to plug with polymer if same reaches a temperature below which polymeric material which is present in the ASO, will freeze out or otherwise deposit on the equipment, which then requires system shut-down for removal of the polymer to make the system operable again.

In the practice of this invention a method is provided for operating an HF catalyst purification unit so as to produce an HF stream of high purity with respect to ASO and to produce an ASO stream with a low HF content. This is advantageously accomplished by contacting ASO from the lower region of the purification unit with a vaporous isoparaffin and circulating the ASO within the lower region and through a stand pipe situated in the lower section of the purification unit.

The principal objects of the present invention are: to provide a method and apparatus for purifying HF by removing ASO therefrom and to minimize loss of HF in the ASO; to provide such an apparatus which has a reduced tendency to plug with polymer in an eductor through which collected ASO is circulated; to provide such an apparatus which will operate longer between maintenance periods; to provide such an apparatus which is combined in a single unit and thereby more compact; to provide such an apparatus and method which effects more intimate contact between a vaporous isoparaffin and collected ASO for stripping HF therefrom; and to provide such an apparatus and method which is efficient in operation and well adapted for its intended use.

Other objects and advantages of the present invention will become apparent from the following description taken in connection with the accompanying drawings wherein are set forth by way of illustration and example certain embodiments of the present invention.

FIG. 1 is a diagrammatic view of an HF alkylation catalyst purification apparatus with a purification column or HF rerun column shown in section.

Referring more in detail to the drawings:

As required, detailed embodiments of the present invention are disclosed herein, however, it is to be understood that the disclosed embodiments are merely exemplary of the invention which may be embodied various forms. Therefore, specific structural and functional details disclosed herein are not to be interpreted as limiting but merely as a basis for the claims and as a representative basis for teaching one skilled in the art to variously employ the present invention in virtually any appropriate detailed structure.

The reference numeral 1 designates an alkylation reactor. An olefin feedstream is introduced through a conduit 2 and an isoparaffin feed stream is introduced through a conduit 3. The olefin feed generally comprises one or more olefins preferably having from 2 to 5 carbon atoms while the isoparaffin stream generally comprises isobutane and/or isopentane. Typically, the olefin feed comprises a mixture of propylene and butylenes while the isoparaffin is comprised primarily of isobutane. A catalyst, preferably hydrogen fluoride (HF), is introduced into the reactor 1 for carrying out of the alkylation process with fresh catalyst being supplied from a source 5 through a conduit 6 and recycled HF can be supplied to the reactor through conduit 7. Effluent from the reactor 1 is conducted to a settler 8 by conduit 9 in which a liquid phase separation is made between the acid and hydrocarbons. The hydrocarbon phase is removed through a conduit 11 and conducted to fractionation means 12. Fractionation means 12 can be one or more conventional fractionators. The fractionator 12 is operated to produce a bottoms alkylate product stream which is removed through a conduit 14, an overhead propane stream which is removed through a conduit 15, a normal butane stream which is removed through a side conduit 16 and vaporous isobutane stream which is removed through a side conduit 17 for a purpose described below. Reflux means 15' and reboil means 14' are shown on the fractionator. Liquid isobutane is removed via conduit 17' and recycle to alkylation reactor 1.

The acid phase containing ASO is removed from the settler 8 through a conduit 19 whereby a portion of the stream can be recycled directly to the reactor 1 by a conduit 20 which is shown as connected to the conduit 6. The remaining portion of the acid stream is passed through a conduit 21 to an acid purification column 22. A valve 23 and a heater 24 are connected to the conduit 21 to control the flow rate of and heat the stream to at least partially vaporize same before same enters the column 22. The conduit 21 is connected to an inlet 25 which opens into the interior of the column 22.

A liquid hydrocarbon or isoparaffin reflux is preferably introduced into the upper region of the column 22 through the conduit 17 which has a condenser 27 and valve 28 therein with the valve controlling flow rate and the condenser condensing vaporous isoparaffin from the fractionator 12 to a liquid isoparaffin. If desired, liquid isobutane from conduit 17' can be used as reflux supplied to conduit 17 for column 22. Preferably, the isoparaffin from the fractionator 12 is isobutane. The conduit 17 is connected to an inlet 29 which opens into the column 22 in the upper region thereof. An outlet 31 is in communication with an upper region of the column 22 and is connected to the conduit 7 whereby vaporous isoparaffin and HF are passed back to the reactor 1 for reuse. If desired, this stream of fluid in conduit 31 can be liquefied prior to returning it to reactor 1.

The column 22 is generally vertically disposed and is comprised of an upper chamber or zone 34 and a lower chamber or zone 35 which is sometimes referred to as a leg. A plurality of suitable liquid-vapor contact means such as bubble trays 37 are mounted in the upper chamber 34 and are in spaced apart relation having through openings 38 to allow vapor to pass through the trays for intimate contact with liquid flowing thereover. Downcomers 39 provide communication between adjacent trays. Preferably, the inlet 25 is positioned between adjacent trays 37 with the position being determined by operating parameters and the particular liquid being introduced into the upper chamber 34 from the settler 8. The leg 35 is elongate and has mounted therein a stand pipe 41 with opposite ends having openings adjacent thereto. In the illustrated structure the lower disposed portion of the stand pipe 41 has an opening 42 with the end of the stand pipe preferably being flared or belled. A nozzle 43 is directed toward the opening 42 and into the stand pipe 41 for a purpose to be later described. Preferably, the upper end 44 of the stand pipe 41 has openings 45 directed generally normal to the longitudinal axis of the stand pipe 41 whereby fluid discharged from openings 45 at the end 44 are directed so that the fluid will flow against the side wall of the column 22, rather than upwardly to impinge on one of the trays 37. Preferably baffles 47 are secured within the leg 35 and are in spaced apart relation providing a circuitous flow path downwardly through the leg 35 to a lower portion thereof wherein ASO is collected during operation. An outlet 48 communicates with the interior of the leg 35 and provides an outlet for ASO which is passed through a conduit 49 which is connected to the outlet 48. Preferably, suitable level control means are provided to automatically control the level of ASO in the leg 35 and as shown a controller 50 is operable to sense the liquid level of ASO in the leg 35 and control a valve 51 to regulate the flow of ASO through the conduit 49.

Vaporous isoparaffin is introduced into the lower portion of the leg 35 so that same will contact the ASO that is collected in the leg 35 and flowing downwardly through the leg 35. In a preferred embodiment of the present invention, two points of vaporous isoparaffin introduction are provided but it is to be understood that any number can be used. As shown, two inlets are provided, one being the nozzle 43 and the other being an inlet 53 which are connected to a source 54 of isoparaffin which can be a separate source or from conduits 17 and/or 17'. As shown, both the inlet 53 and the nozzle 43 are connected in a similar manner to the source 54 by conduits 55 and 56, respectively, which are in turn connected to an outlet conduit 57 which is connected to the source 54. Preferably, flow control means and heating means are connected in the conduits 55 and 56 to regulate the flow rate of and to heat the isoparaffin to a temperature sufficient to vaporize the isoparaffin and to produce desired operating temperature. A feed rate controller 58 senses the feed rate and in turn controls a valve 59 to regulate the feed rate at a predetermined amount. A heater 60 is also connected to the conduit 56 and has control means 61 operable to sense the temperature of the isoparaffin and regulate same at a predetermined temperature. Heat is supplied from a source 62 such as steam with the rate of steam introduction to the heaters 60 being regulated by valves 63 which are operably connected to the temperature controllers 61.

The present invention is more fully understood by a description of the operation thereof. The HF catalyst and entrained ASO is introduced into the column 22 through the inlet 25. Vaporous isoparaffin, preferably isobutane, is introduced through the inlet 53 and the nozzle 43 with the vapor flowing upwardly through the leg 35 and into the upper chamber 34 with same intimately contacting the downwardly flowing liquid HF containing ASO with the vaporous isobutane stripping the HF and carrying same upwardly into the upper region of the upper chamber 34 for exhaust through the outlet 31. Liquid isoparaffin, preferably isobutane for reflux, is introduced through the inlet 29 for downward flow through the upper chamber to maintain the operating temperature of the column 22 within predetermined limits. The ASO continues to flow downwardly through the upper chamber 34 and still has slight amounts of HF therein. The ASO flowing downwardly into the leg 35 and is collected in a lower region of the leg 35. As shown, the inlet 53 and nozzle 43 are below the liquid level of the ASO in the leg 35 whereby introduction of the vaporous isoparaffin effects contact between same and the collected ASO. The isoparaffin further strips HF from the collected ASO with the HF and vaporous isoparaffin flowing upwardly through the column 22. Intimate contact is also effected with the ASO and the isoparaffin as the ASO flows downwardly across the baffles 47 for further stripping of HF therefrom. The nozzle 43 forms an eductor with the opening 42 of stand pipe 41 whereby the upwardly directed vaporous isoparaffin effects upward flow of ASO through the stand pipe 41 and out through the openings 45 at the end 44 to effect circulation of the ASO within the leg 35 so that the ASO has increased contact for HF removal therefrom with the vaporous isoparaffin. Because the vaporous isoparaffin is heated and the stand pipe 41 is positioned within the heated leg 35, the stand pipe 41 is maintained at an elevated temperature to prevent plugging by a polymer. The polymer may plug the stand pipe when same becomes a viscous mass at a temperature above the freezing point and deposit on the stand pipe. As such, the temperature is maintained sufficiently high to prevent freezing of the polymer and also prevent the polymer from being in a condition to otherwise be deposited on the stand pipe. The polymer may be present in and introduced with the HF and ASO through the inlet 25.

A typical operating example is illustrated by the following calculated data.

|  | Invention |
|---|---|
| Used HF Acid (25): | |
| Volume, B/D (a) | 1,080 |
| Temp., ° F., | 285 |
| Composition, Wt. % | |
| HF | 90.0 |
| iC$_4$ | 3.1 |
| Acid Sol. Oils (ASO) | 5.5 |
| H$_2$O | 1.4 |
| Isobutane Vapor: | |

-continued

|  | Invention |
|---|---|
| VIA (56) | |
| Vol. B/D (a) | 480 |
| Temp., ° F., | 430 |
| VIA (55) | |
| Vol., B/D | 240 |
| Temp., ° F., | 430 |
| Reflux Isobutane Liquid (29): | |
| Vol., B/D | 72 |
| Temp., ° F., | 110 |
| ASO Yield (48): | |
| Vol., B/D, (b) | 34.4 |
| Contains HF., Lbs/day | 200 |
| Eductor (42) Temp., ° F., | 430 |
| ASO via Eductor | |
| Volume, B/D, | 300 |
| Temp., ° F., | 318 |
| Time of Operation Before Eductor | |
| Plugs with Polymer, Days (c) | 180 |

A vapor stream (remainder from feed) of regenerated HF (contains iC$_4$) is removed via 31 at 265° F. The tower is operated at 115 psig, a top temperature of 265° F. and a bottom temperature of 320° F.

(a) Measured as liquid.
(b) Contains 200 Lb. HF and 1,150 Lb./day water.
(c) Estimated.

As described above, the stand pipe 41 has a reduced tendency to have a buildup or plugging with polymer because same is operated at an elevated temperature above the freezing or deposition point of the polymer. Also, the stand pipe 41 and the nozzle 43 effect circulation of the ASO within the leg 35 to remove most of the remainder of the HF from the ASO. The ASO is exhausted through the outlet 48 and the conduit 49 to other processing equipment as is known in the art.

It is to be understood that while I have illustrated and described certain forms of my invention, it is not to be limited to the specific form or arrangement of parts herein described and shown.

What is claimed and desired to be secured by Letters Patent is:

1. In an olefin and isoparaffin alkylation process employing an HF catalyst, in which effluent from a reaction zone is passed to a settling zone to separate an acid stream containing HF and acid soluble oil which stream is then purified by separating the HF and acid soluble oil by a process comprising the steps of:
    a. introducing said acid stream into the intermediate region of an upper chamber of a purification column, said column comprising said upper chamber and a lower leg in communication with said chamber;
    b. introducing the isoparaffin as a liquid into an upper region of said chamber as a reflux;
    c. introducing the first portion of vaporous isoparaffin into said lower region of a leg, said vaporous isoprafffin flowing upwardly through said leg and said upper chamber to strip HF from said acid stream
    d. intimately contacting said first portion of vaporous isoparaffin with acid soluble oil collected in said leg;
    e. introducing a second portion of said vaporous isoparaffin into an eductor positioned at the bottom of a stand pipe in said leg to provide circulation of acid soluble oil upwardly therethrough and back into said leg;
    f. removing a stream containing vaporous isoparaffin and purified HF from the top of said upper chamber; and
    g. recovering acid soluble oil substantially free of entrained HF from the lower portion of said leg.

2. The process as set forth in claim 1 including:
    a. heating said acid stream before introducing same into said upper chamber; and
    b. controlling the level of acid soluble oil in said leg.

3. The process as set forth in claim 2 wherein:
    a. said liquid isoparaffin and said vaporous isoparaffin comprise isobutane.

4. The process as set forth in claim 2 including:
    a. heating an isoparaffin to a temperature to form said vaporous isoparaffin, said temperature being high enough to maintain said stand pipe at a temperature above the temperature at which said polymer contained in said stream would be deposited on said stand pipe.

* * * * *